United States Patent [19]

Segal et al.

[11] Patent Number: 4,869,263
[45] Date of Patent: Sep. 26, 1989

[54] DEVICE AND METHOD FOR MEASURING VOLUMETRIC BLOOD FLOW IN A VESSEL

[75] Inventors: Jerome Segal; Paul D. Corl, both of Palo Alto; Wayne C. Haase, Mountain View, all of Calif.

[73] Assignee: Cardiometrics, Inc., Mountain View, Calif.

[21] Appl. No.: 152,098

[22] Filed: Feb. 4, 1988

[51] Int. Cl.$^4$ ............................................. A61R 5/02
[52] U.S. Cl. .................................. 128/692; 128/713; 128/662.06; 128/663.01; 128/673
[58] Field of Search ............................. 128/660–663, 128/691–694, 713, 772, 656–658, 344, 672–675, 661.07–661.09, 661.10, 662.01, 662.06, 663.01; 604/96–103

[56] References Cited

U.S. PATENT DOCUMENTS

| | | | |
|---|---|---|---|
| 4,319,580 | 5/1982 | Colley | 128/661 |
| 4,589,419 | 5/1986 | Laughlin et al. | 128/663 |
| 4,605,009 | 8/1986 | Pourcelot et al. | 128/660 |
| 4,616,652 | 10/1986 | Simpson | 128/657 X |
| 4,637,401 | 1/1987 | Johnston | 128/663 |
| 4,665,925 | 5/1987 | Millar | 604/96 X |
| 4,721,115 | 1/1988 | Owens | 128/713 |
| 4,722,347 | 2/1988 | Abrams et al. | 128/661 X |
| 4,733,669 | 3/1988 | Segal | 128/663 |

Primary Examiner—Lee S. Cohen
Assistant Examiner—Angela D. Sykes
Attorney, Agent, or Firm—Flehr, Hohbach, Test, Albritton & Herbert

[57] ABSTRACT

Device for measuring volumetric blood flow in a vessel comprising a catheter having proximal and distal extremities. A balloon is carried by the distal extremity of the catheter. A balloon inflation lumen is carried by the catheter and is in communication with the balloon. A toroidal ultrasonic transducer is carried by the catheter and is spaced proximally of the balloon. Electrical circuitry is provided for supplying electrical energy to the transducer. The transducer produces a large substantially uniform beam of ultrasonic energy to illuminate a vessel of approximately three centimeters in diameter with the ultrasonic energy.

17 Claims, 3 Drawing Sheets

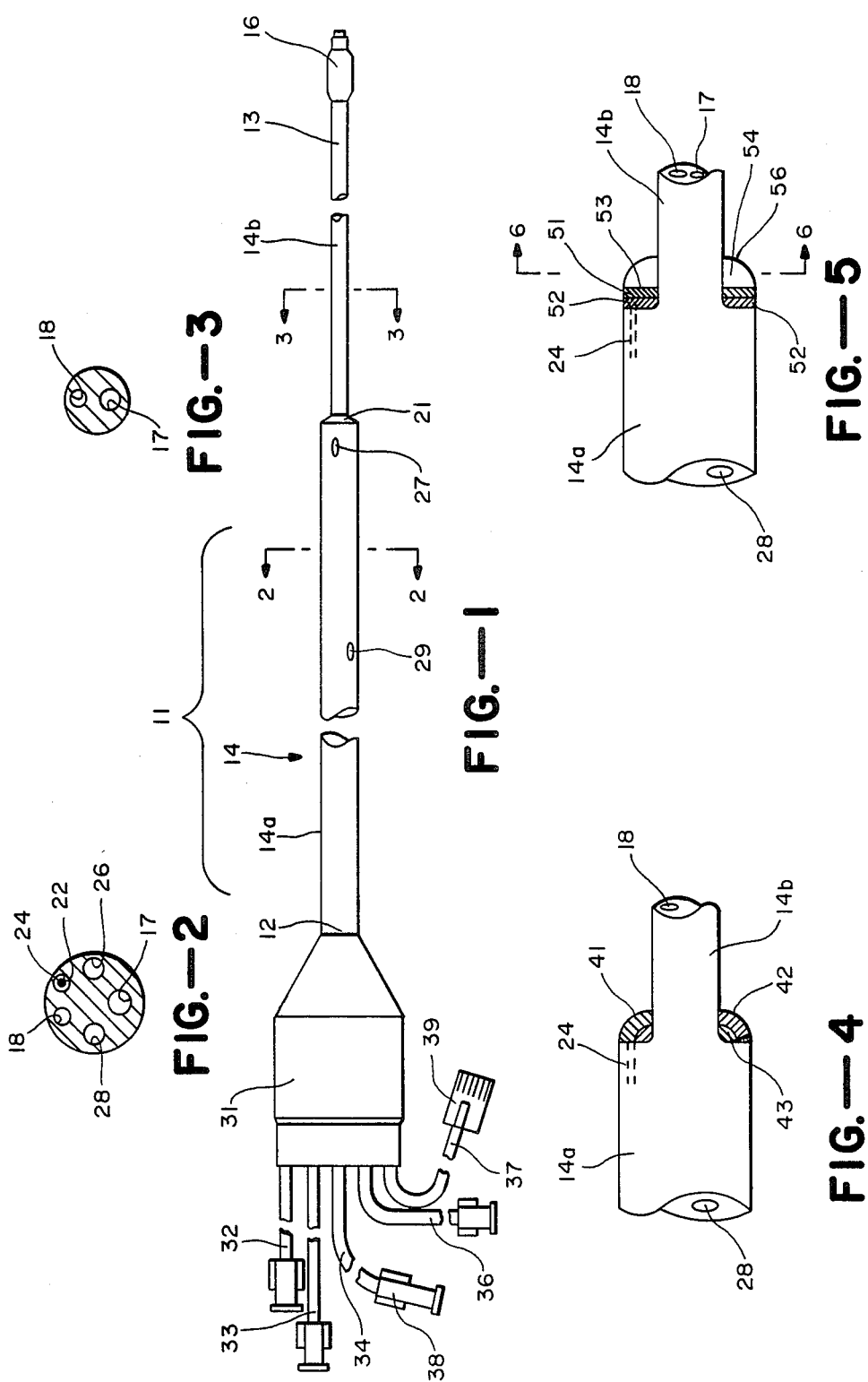

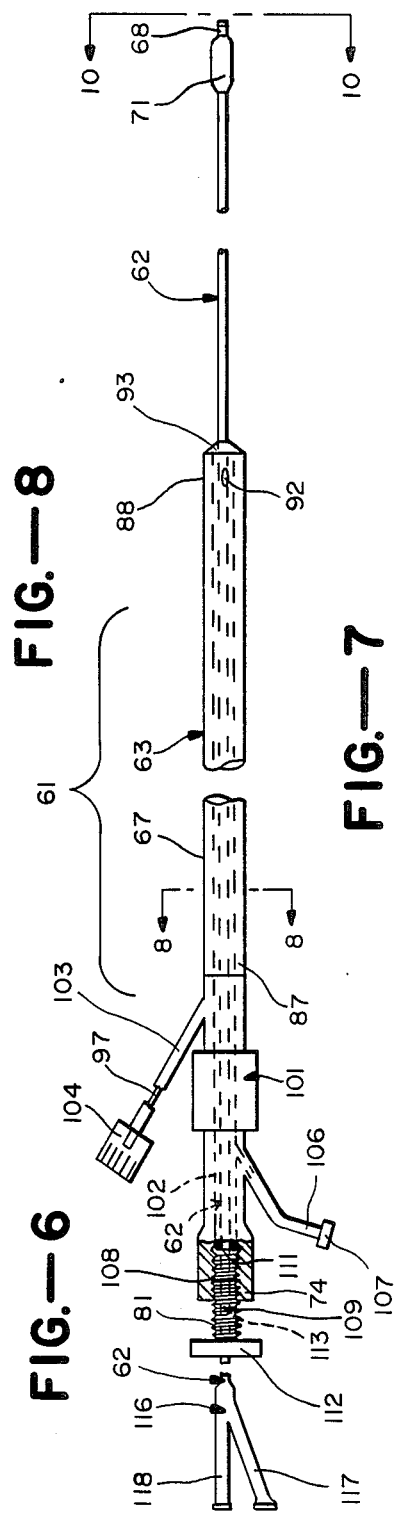
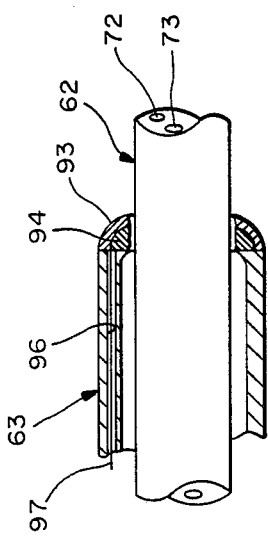
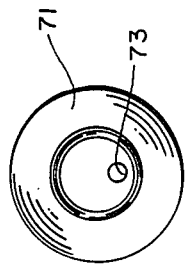

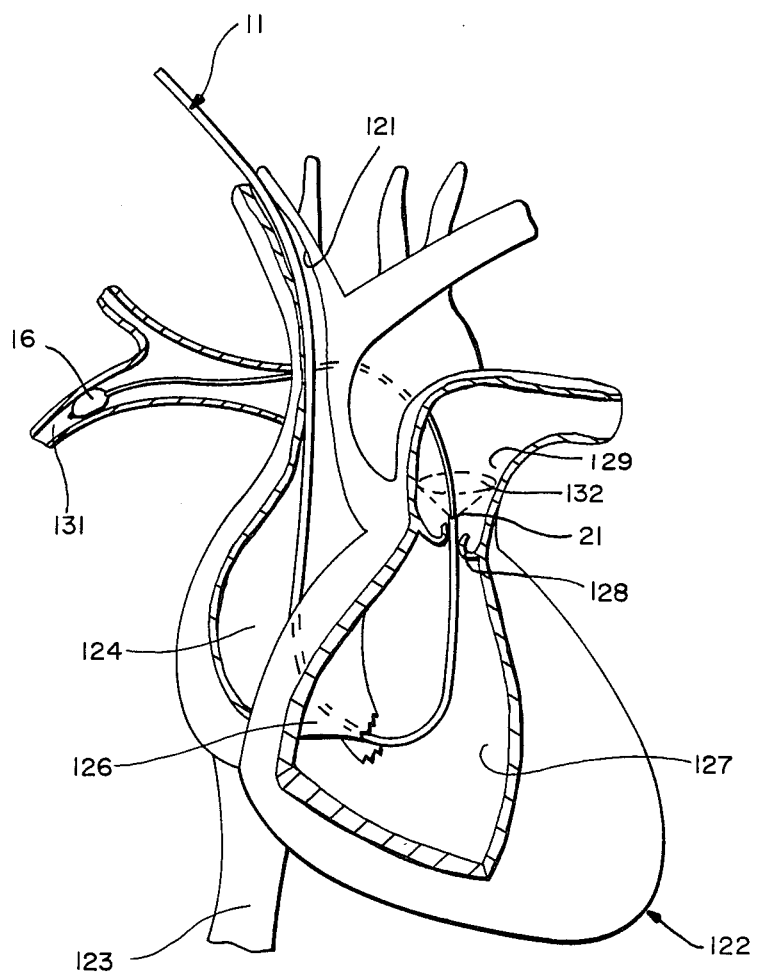
FIG.—11

DEVICE AND METHOD FOR MEASURING VOLUMETRIC BLOOD FLOW IN A VESSEL

This invention relates to a device and method for measuring volumetric blood flow in a vessel and more particularly to such a device and method which utilizes ultrasonics.

Diagnostic catheters have previously been provided for measuring cardiac output and pressures utilizing either thermodilution, dye dilution or oxygen consumption methods. More recently intravascular catheters have been developed which measure instantaneous flow velocity utilizing doppler ultrasonic transducers to measure the "doppler shift" created by the movement of red blood cells within the blood vessel of interest. Typically, the doppler catheter utilized in such systems have been capable of measuring blood flow velocity within a small sample volume contained within the blood vessel. Volumetric flow could not be accurately determined utilizing such doppler systems because additional information such as vessel dimension, flow profile and incidence angle between the ultrasonic beam and the direction of flow must be ascertained in order to accurately determine volumetric flow. In co-pending application Ser. No. 036,796 filed on Apr. 10, 1987, pending, there is disclosed an apparatus, system and method for measuring volumetric flow of blood in a vessel which discloses a catheter and guide wire transducer apparatus and system which can be utilized in a method for measuring volumetric blood flow in small blood vessels. Typically this is accomplished by the creation of a large uniform beam in the far field of a relatively small transducer. However, it has been found that there is a need for illuminating vessels of larger diameters which cannot be readily accomplished with the apparatus of Ser. No. 036,796. There is therefore a need for a new and improved device and method for measuring volumetric blood flow in a vessel. More specifically there is a need for measuring cardiac output in man by illuminating the main pulmonary artery which receives the total blood flow of the heart.

In general, it is an object of the invention to provide a device and method for measuring volumetric blood flow in a vessel in which a large uniform beam is created.

Another object of the invention is to provide a device and method of the above character in which it is unnecessary to angularly position the transducer.

Another object of the invention is to provide a device and method of the above character capable of measuring volumetric blood flow in a vessel independent of position of the transducer within the vessel.

Another object of the invention is to provide a device and method of the above character which can be positioned without the use of fluoroscopy by means of a flotation balloon.

Another object of the invention is to provide a device and method of the above character in which independent pulmonary wedge pressure measurements can be made simultaneously with cardiac output measurements.

BRIEF DESCRIPTION OF THE DRAWINGS

Additional objects and features will appear from the following description in which the preferred embodiments are set forth in detail in conjunction with the accompanying drawings.

FIG. 1 is a side elevational view of a catheter incorporating the present invention.

FIG. 2 is a cross-sectional view taken along the line 2—2 of FIG. 1.

FIG. 3 is a cross-sectional view taken along the line 3—3 of FIG. 1.

FIG. 4 is an enlarged view partially in cross-section of the portion of the catheter shown in FIG. 1 and particularly showing the transducer.

FIG. 5 is a view showing the construction of the transducer.

FIG. 6 is a cross-sectional view taken along the line 6—6 of FIG. 5.

FIG. 7 is a side elevational view of a catheter incorporating another embodiment of the present invention.

FIG. 8 is a cross sectional view taken along the line 8—8 of FIG. 7.

FIG. 9 is a view of a portion of the catheter show in FIG. 7 partly in cross section.

FIG. 10 is an end elevational view of the transducer shown in FIG. 9.

FIG. 11 is a view of a catheter incorporating the present invention, in place, within the heart.

DESCRIPTION OF THE PREFERRED EMBODIMENTS

In general, the device for measuring volumetric blood flow in a vessel is comprised of an elongate catheter having proximal and distal extremities with an inflatable balloon carried by the distal extremity of the same. A toroidal transducer is carried by the catheter spaced from the distal extremity and is of a size and configuration which creates a large uniform beam. In order to achieve the large uniform beam, the transducer itself can have a convex configuration in a direction facing the distal extremity of the catheter or, alternatively, the transducer can be provided with a convex lens serving to spread the beam to create the large uniform field. In an alternative embodiment, the catheter can be comprised of first and second coaxial catheter members, with the first member carrying the ultrasonic transducer and the second member carrying the inflatable balloon.

More specifically as shown in FIGS. 1-5, the device for measuring volumetric blood flow in a vessel consists of an elongate catheter 11 having proximal and distal extremities 12 and 13. The catheter 11 can have a suitable length as, for example, 100 centimeters. The catheter is formed of a flexible elongate member 14 of a suitable material such as plastic which is provided with a portion 14a which is approximately 85 centimeters in length and a portion 14b which is approximately 15 centimeters in length. The flexible elongate member 14 can be formed in a suitable manner such as by extrusion. The portion 14a is provided with five lumens extending therethrough whereas a portion 14b is provided with two lumens extending therethrough. An inflatable balloon 16 is provided adjacent the distal extremity of the catheter 11 and can be formed integral with the flexible elongate member 14 or as is well known to those skilled in the art can be formed separately on the distal extremity of the catheter. The proximal portion 14a of the flexible elongate member 14 can have a suitable diameter as, for example, 0.098 inches whereas the portion 14b can also be of a suitable diameter as, for example, 0.060 inches.

With respect to the lumens hereinbefore described, a distal lumen 17 is provided having a diameter of approximately 0.020 inches which extends from the proximal extremity 12 to the distal extremity of the catheter and exits through the distal extremity 14b of the catheter. There is also provided a balloon inflation lumen 18 which also extends from the proximal extremity to the distal extremity of the catheter. The distal extremity is in communication with the interior of the balloon 16 to permit inflation and deflation of the balloon.

A toroidal transducer 21 is carried by the flexible elongate member 14 adjacent the distal extremity of the portion 14a. A wire lumen 22 is provided in the portion 14a for receiving the electrical conducting wires 24 connected to the transducer 21. The portion 14a of the flexible elongate member 14 is provided with a pulmonary artery lumen 26 which is in communication with a port 27 provided a suitable distance, as for example, adjacent the distal extremity of the portion 14a and spaced approximately 14 centimeters from the tip of the distal extremity of the catheter 11. The portion 14a is also provided with a right ventricular lumen 28 which is in communication with a right ventricular port 29 opening through the side of the portion 14a as shown particularly in FIG. 1. The right ventricular port 29 is located approximately 5 centimeters proximal of the pulmonary artery port 27 on the catheter 11. The wire lumen 22 can have a suitable diameter such as 0.012 inches whereas the pulmonary artery lumen and the right ventricular lumen 26 and 28 can have similar dimensions such as 0.018 inches. The proximal extremity of the catheter 11 is provided with a fitting 31 which includes five extension members 32, 33, 34, 36 and 37. Extension members 32, 33, 34, and 36 are provided with suitable fittings 38, as for example, Luer-type fittings on their proximal extremities. Extension 37 is provided with an electrical connector 39 which is connected to conducting wires 24. The distal extremities of the tubular extensions 32, 33, 34, 36 and 37 are mounted in a fitting 31 so that they are in communication with the five lumens provided in the portion 14a of the flexible elongate member 14. Thus by way of example, the extension 32 can be in communication with the lumen 17, extension 33 in communication with the lumen 18, extension 37 in communication with the lumen 22 and the extensions 34 and 36 in communication with the lumens 26 and 28 respectively.

As shown in FIG. 1, the transducer 21 is mounted at the transition between the portion 14a and 14b of the flexible elongate member 14. As shown particularly in FIG. 4, the transducer 21 is formed as a toroid and has a convex frontal surface 41 which faces in a direction axially of the flexible elongate member 14 and towards the distal extremity of the catheter 11. The transducer 21 is coated with a polyurethane coating 42 and is backed by and secured to the distal extremity of the portion 14a by an epoxy-microsphere backing material 43. The transducer 21 is of a size and configuration which enables it to create a large uniform beam capable of encompassing a vessel at least approximately 3 centimeters in diameter. The transducer 21 is coupled by the wires 24 extending through the wire lumen 22 to circuitry of the type disclosed in co-pending application Ser. No. 036,796 filed on Apr. 10, 1987.

An alternative embodiment of the invention is shown in FIGS. 5 and 6 in which a transducer 51 is provided in the same location as the toroidal transducer 21 but which, rather than being convex in shape, is disc-shaped having a planar forwardly facing surface 53. The transducer 51 is secured to and backed up by an epoxy-microsphere backing material 52.

In order to obtain a large uniform beam from the transducer 51 which will encompass a vessel of at least approximately 3 centimeters in diameter, a lens 54 of suitable material such as plastic is mounted upon the surface 53 of the transducer 51. The lens 54 as shown in FIG. 5 is provided with a convex surface 56 which faces forwardly of the catheter toward the distal extremity of the same. The lens 54 will cause the focused beam supplied by the transducer 51 to spread radially enabling the transducer 51 to create a large uniform field for flow measurement in large vessels, as for example, 3 centimeters in diameter. In the present embodiment of the invention, the transducer 21 is in a fixed location at a point approximately 14 centimeters proximal to the distal tip of the catheter 11 and thus there is a fixed relationship distance with respect to the balloon 16 and the transducer 21.

Still another embodiment of the device and method for measuring volumetric blood flow in a vessel is shown in FIGS. 7–10 in which there is shown a pulmonary artery catheter assembly 61 which consists of two coaxial catheters 62 and 63 in which the inner catheter 62 is slidably mounted in the otter catheter 63 for movement axially of the catheter assembly 61. The inner catheter 62 consists of a flexible elongate member 66 formed of a suitable material such as an extruded plastic which is provided with proximal and distal extremities 67 and 68 respectively. A latex balloon 71 is carried by the distal extremity 68 and preferably is formed of a separate balloon which is bonded to the distal extremity in a suitable manner such as by an adhesive. The flexible elongate member 66 is provided with lumens 72 and 73 extending substantially the entire length thereof in which lumen 72 can be identified as the balloon inflation and deflation lumen and which is in communication with the interior of the balloon 71. The other lumen 73 can be identified as the distal lumen and has the size of approximately 0.020 inches and lumen 72 has a size of approximately 0.008 inches. The exterior of the flexible elongate member 66 can have a suitable exterior dimension such as 0.060 inches. The distal lumen 73 extends through the length of the flexible elongate member 66 and is open at the distal extremity to facilitate the making of pressure measurements.

The outer catheter 63 consists of a flexible elongate member 86 formed with a suitable material such as plastic and has a suitable exterior diameter such as 0.098 inches. The flexible elongate member 86 has proximal and distal extremities 87 and 88. It also is provided with a large bore lumen 89 extending the length thereof which has a suitable diameter such as 0.070 inches and is particularly sized in such a manner so that there is formed an annular space 91 between the exterior surface of the flexible elongate member 66 and the interior of the flexible elongate member 86 which can serve as a pulmonary artery pressure lumen. The annular space 91 is in communication with a pulmonary artery port 92 provided in the side wall of the flexible elongate member 86 adjacent the distal extremity 88 thereof.

A toroidal piezoelectric ultrasonic transducer 93 is mounted on the distal extremity of the outer catheter 63. The transducer 93 is formed in the same manner as the transducer 21 in FIGS. 1–4. As described therein, the transducer 93 is formed as a toroid having a convex surface facing towards the distal extremity of the inner catheter 62. An epoxy backing material 94 of the type hereinbefore described is provided behind the transducer 93. A small wire lumen 96 is provided in the side wall of the flexible elongate member 86 and receives the wires 97 connected to the transducer 92.

A fitting 101 is mounted on the proximal extremity 87 of the flexible elongate member 86 forming a part of the outer catheter 63 and is formed of a suitable material such as plastic. The fitting 101 is provided with a central bore 102 which is in communication with the lumen 89 provided in the outer catheter 63. The fitting 101 is provided with a leg 103 through which the wires 97 extend and which are connected to an electrical connector 104. The fitting 101 is provided with another leg 106 which is provided with a Luer-type fitting 107 and has a passage which is in communication with the main bore 102. The fitting 101 is provided with a threaded bore 108 which is coaxially aligned with the bore 102. A threaded shaft 109 is threaded into the threaded bore 108. The shaft 109 is provided with a conical distal extremity which is adapted to come in engagement with an O-ring 111 disposed within the threaded bore 108 and encircling the threaded bore. The threaded shaft 109 is provided with a knob 112 to facilitate rotation of the shaft. The threaded shaft is provided with a bore 113 extending axially thereof and which is in communication with the bore 102. The inner catheter 62 is adapted to be inserted into and withdrawn from the bore 113. A two-armed adapter or fitting 116 is mounted on the proximal extremity 67 of the catheter 62. The side arm 117 is in communication with the balloon inflation lumen 72 and the central arm 118 is in communication with the distal lumen 73.

Operation and use of the embodiment of the device shown in FIGS. 1–3 for measuring volumetric blood flow in a vessel and, more specifically, cardiac output may now be briefly described as follows. The catheter 11 can be inserted into the human body in a substantially conventional manner. The catheter 11 is connected to the appropriate monitoring equipment (not shown). The catheter 11 is then introduced by a percutaneous technique through a suitable needle or sheath (not shown) into a large vein. The catheter 11 is then gently advanced until the tip has been advanced into the superior vena cavae 121 of the heart 122 as shown in FIG. 11. Alternatively, if desired, the catheter 11 can be introduced into the inferior vena cavae 123. At this point, the balloon 16 is inflated with air or carbon dioxide to an appropriate volume of 1.5 cc. The balloon and catheter distal extremity are thereafter floated through the right atrial chamber 124 through the tricuspid valve 126, into the right ventricle 127 of the heart and then through the pulmonary valve 128, through the main pulmonary artery 129 and out into the distal pulmonary artery 131. During the positioning of the catheter 11, the standard pressure measurements can be made by sensing the blood pressure through the lumen 17. In this way, the right atrial pressure, the right ventricular pressure, pulmonary artery pressure and pulmonary capillary wedge pressure can be measured. Pulmonary artery pressure may be measured through the port 27, in communication with the lumen 26. Right ventricular pressure may be simultaneously measured through port 29 in communication with the lumen 28. Since the port 27 is adjacent the transducer 21, the presence of a pulmonary artery waveform via lumen 26 confirms the position of the transducer 21 within the main pulmonary artery 129. Placement of the transducer 21 within the main pulmonary is critical for measurement of total cardiac output, since the entire cardiac output is ejected only through the main pulmonary artery. Monitoring the right ventricular pressure through the port 29 in communication with the lumen 28, while simultaneously monitoring the pulmonary artery pressure through the port 27 via the lumen 26 assures that the transducer 21 is located within the main pulmonary artery 129 and not in a more distal pulmonary artery branch 131. If the transducer 21 were located more distally in the pulmonary artery, the right ventricular port 29 would also reveal a pulmonary artery waveform, indicating that the catheter 11 needed to be withdrawn slightly to place the transducer 21 within the main pulmonary artery. Alternatively, should the right ventricular waveforms be noted through both ports 27 and 29, this would indicate that the transducer 21 needs be advanced slightly into the main pulmonary artery for accurate cardiac output measurements to be obtained.

When an ultrasonic measurement of cardiac output is desired, electrical energy is supplied to the transducer at the proper frequency, as for example, 10 MHz As soon as this occurs, the crystal converts the high frequency energy to ultrasonic energy to create a large uniform cone-shaped beam 132 of ultrasound which beam extends forwardly in the vessel as shown in FIG. 11 and encompasses the entire main pulmonary artery 129. The first moment detection technique described in the co-pending application Ser. No. 036,796 filed on Apr. 10, 1987 is utilized to measure absolute flow through this sample volume which is being monitored by the use of the large uniform beam of ultrasound. The lumen 17 extending through the distal extremity of the catheter is used to make pulmonary capillary wedge pressure measurements, simultaneous with pulmonary artery pressure measurements via lumen 28, right ventricular pressure measurements via lumen 26 and cardiac output measurements via the ultrasonic transducer 21 and appropriate circuitry.

By utilizing a large uniform beam to encompass the interior of the entire main pulmonary artery, the information obtained from the uniform beam can be utilized with the first moment detection technique in connection with the computational constant previously described in co-pending application Ser. No. 036,796 filed on Apr. 10, 1987, to give a true volumetric flow through the sample volume in the main pulmonary artery. The method of the present invention can make such volumetric flow measurements with a single transducer having the particular convex shape to provide a large uniform beam of isonification without knowledge of the size of the vessel, the angle of incidence between flow and the ultrasonic beam, the velocity profile within the vessel, or the exact location of the transducer 21 within vessel of interest.

Operation use of the embodiment of the invention shown in FIGS. 5 and 6 is very similar to that hereinbefore described with the embodiment shown in FIGS. 1–4.

Operation and use of the catheter assembly 61 shown in FIGS. 7–10 is as follows. The knob 112 is unscrewed to allow easy withdrawal of the catheter 62 into the body of the outer catheter 63 until the balloon 71 is in proximity of the transducer 93. The knob 112 may now be tightened, compressing the O-ring 111 and preventing backflow of blood from the annular space 91. The entire catheter assembly 61 can now be inserted into the human body in the conventional manner previously described. The catheter 61 is then gently advanced until the tip has been advanced into the superior vena cavae 121 or the inferior vena cavae 123 of the human heart 122. At this point, the balloon 71 is inflated, as previously described, and the catheter and distal extremity are thereafter floated through the right atrium 124, tricuspid valve 126, right ventricle 127, pulmonary valve 128 and into the main pulmonary artery 129 in the manner previously described.

At this point, the pulmonary artery waveform tracings may be simultaneously obtained through the distal lumen 73 and the proximal pulmonary artery port 92 in communication with the annular space 91. The knob 112 may be unscrewed, and the inner catheter 62 with the balloon 71 still inflated may be advanced into the distal pulmonary artery 131 while the outer catheter 63 is held in place, thus keeping the transducer 93 in place within the main pulmonary artery 129. The catheter 62 is advanced until a pulmonary capillary wedge pressure waveform is obtained via the distal lumen 73. At this point, the knob 112 may be retightened, preventing a backflow of blood from the port 92 via the annular space 91. At this point, simultaneous pulmonary capillary wedge pressure, and pulmonary artery pressure are available via distal lumen 73 and annular space 91 respectively. The principal advantage of the present embodiment is that the distance between the balloon 71 and the transducer 93 carried on the distal extremity of the outer catheter 63 can be varied merely by shifting the position of the inner catheter 62 with respect to the outer catheter 63.

Accurate flow measurements may now be obtained by connecting the catheter assembly 61 to the electrical system which is disclosed in co-pending application Ser. No. 036,796 filed on Apr. 10, 1987. By varying the distance between the balloon 71 and the transducer 93 it is possible to obtain an accurate measurement of the distal pulmonary capillary wedge pressure where the balloon is positioned, and still retain the transducer 93 in the main pulmonary artery for accurate cardiac output measurements. The pressure which is measured by the pulmonary artery port 92 indicates the location of the transducer. The distal pressure which is measured at the distal extremity just beyond the balloon 71 indicates the location of the balloon. The exact position of the pulmonary artery port 92 is important in that the transducer should be located just distal to the pulmonary valve within the main pulmonary artery 129. This can be readily ascertained because as the pulmonary artery port passes through the pulmonary valve there will be a change in waveform to indicate the proper location for the transducer 93.

Thus it can be seen that it is possible to make cardiac output measurements in the main pulmonary artery and simultaneously make pressure measurements distal of the main pulmonary artery at distances which need not be fixed with respect to the transducer 93. In this way it is possible to compensate for the different distances between main pulmonary artery and capillary wedge positions which occur in the anatomy of various persons. With the embodiment shown in FIG. 1 it is not possible to accommodate the different dimensions which can be encountered in the human anatomy. In addition, the present embodiment makes it possible to eliminate the use of an independent lumen for pressure measurements since the annular space 91 between the catheters 63 and 62 is used for such a measurement.

From the foregoing it can be seen that a pulmonary artery catheter has been provided which permits a measurement of instantaneous cardiac output while utilizing a transducer capable of propagating a large uniform beam within the main pulmonary artery. In addition by utilizing the coaxial construction, independent pulmonary capilliary wedge pressure measurements may be made simultaneously with cardiac output measurements.

What is claimed is:

1. In a device for measuring volumetric blood flow in a vessel, a catheter having proximal and distal extremities, a balloon carried by the distal extremity, a balloon inflation lumen carried by the catheter, a toroidal ultrasonic transducer carried by the catheter spaced proximally of the balloon, means for supplying electrical energy to the transducer, the transducer being provided with means for producing a large substantially uniform beam to illuminate a vessel of approximately three centimeters in diameter with ultrasonic energy.

2. A device as in claim 1 wherein said means for producing a large substantially uniform beam includes a convex construction for said transducer.

3. A device as in claim 1 wherein said transducer operates in the range of 1 to 20 MHz and has an outer diameter ranging from 2 to 5.0 millimeters.

4. A device as in claim 1 wherein said transducer is disc-shaped and wherein said means for producing a large substantially uniform beam is in the form of a convex lens disposed in close proximity to the transducer.

5. In a device for measuring volumetric blood flow in a vessel, a catheter having proximal and distal extremities, a balloon carried by the distal extremity, a balloon inflation lumen carried by the catheter, a toroidal ultrasonic transducer carried by the catheter spaced proximally of the balloon, means for supplying electrical energy to the transducer, the transducer being provided with means for producing a large substantially uniform beam to illuminate a vessel of approximately three centimeters in diameter with ultrasonic energy, said catheter being provided with a transition and with a first portion having a first diameter extending to the transition and a second portion extending from the transition having a second diameter which is less than the diameter of the first portion said transducer being disposed at the transition between the first portion and the second portion.

6. A device as in claim 5 wherein said first and second portions have a fixed axial relationship with respect to each other.

7. A device as in claim 5 wherein said second portion is provided with proximal and distal extremities and wherein a port is provided adjacent the distal extremity and wherein said catheter has a lumen extending therethrough in communication with the distal port.

8. A device as in claim 5 wherein said first portion is provided with proximal and distal extremities and wherein a pulmonary artery port is provided adjacent the distal extremity and wherein said first portion has a lumen extending therethrough in communication with the pulmonary artery port.

9. A device as in claim 5 wherein said first portion is provided with a wire lumen together with electrical conductors disposed in the wire lumen and in contact with the transducer.

10. A device as in claim 5 wherein said second portion is movable axially of the first portion.

11. In a device for measuring volumetric blood flow in a vessel, a catheter having proximal and distal extremities, said catheter being provided with a first portion having a first diameter and a second portion having a second diameter which is less than the diameter of the first portion, said second portion being movable axially of said first portion and having a distal extremity, a balloon carried by the distal extremity of said second portion, a balloon inflation lumen carried by the catheter, a toroidal transducer carried by the catheter spaced proximally of the balloon and means for supplying electrical energy to the transducer, the transducer producing a large substantially uniform beam to illuminate a vessel of approximately three centimeters in diameter.

12. A device as in claim 11 in which the first and second portions are provided by an outer catheter and an inner catheter slidably mounted for axial movement in the outer catheter.

13. A device as in claim 11 wherein said first portion has proximal and distal extremities and wherein a port is provided adjacent the distal extremity of the first portion and wherein said first portion has a lumen extending therethrough in communication with said port.

14. A device as in claim 13 wherein an annular space is provided between the first and second portions, said annular space being in communication with said port.

15. A device as in claim 11 wherein said transducer is disposed at the distal extremity of said first portion.

16. A device as in claim 11 wherein said first portion is provided with a wire lumen together with electrical conductors disposed in the wire lumen and in electrical contact with the transducer.

17. A method for simultaneously measuring cardiac output and pulmonary wedge pressure by positioning a device for measuring volumetric blood flow in a vessel, the device comprising a catheter having proximal and distal extremities, said catheter being provided with a first portion having a first diameter and a second portion having a second diameter which is less than the diameter of the first portion, said second portion being movable axially of said first portion and having a distal extremity, a balloon carried by the distal extremity of said second portion, a balloon inflation lumen carried by the catheter, toroidal transducer carried by the catheter spaced proximally of the balloon and means for supplying electrical energy to the transducer, the transducer producing a large substantially uniform beam to illuminate a vessel of approximately three centimeters in diameter, the method comprising positioning the device such that the distal extremity of the second portion is located in the distal pulmonary artery and measuring pulmonary wedge pressure while the transducer is situated within the main pulmonary artery measuring cardiac output.

* * * * *